United States Patent [19]

Smith et al.

[11] 4,113,877

[45] Sep. 12, 1978

[54] SUBSTITUTED 2-AMINOMETHYLPHENYL SULFAMATES

[75] Inventors: Robert L. Smith, Lansdale; Gerald E. Stokker, Gwynedd Valley; Edward J. Cragoe, Jr., Lansdale, all of Pa.

[73] Assignee: Merck & Co., Inc., Rahway, N.J.

[21] Appl. No.: 833,930

[22] Filed: Sep. 16, 1977

[51] Int. Cl.$^2$ .................. A61K 31/095; C07C 141/16
[52] U.S. Cl. ................................. 424/303; 260/456 A
[58] Field of Search ..................... 260/456 A; 424/303

[56] References Cited

U.S. PATENT DOCUMENTS

| 2,839,562 | 6/1958 | Wegler et al. | 260/456 A |
|---|---|---|---|
| 3,082,238 | 3/1963 | Dunbar | 424/303 |
| 3,560,521 | 2/1971 | Milkowski et al. | 260/456 A |
| 3,794,734 | 2/1974 | Cragoe et al. | 424/330 |
| 4,029,816 | 6/1977 | Cragoe et al. | 424/316 |

FOREIGN PATENT DOCUMENTS

| 702,226 | 1/1965 | Canada | 260/456 A |
|---|---|---|---|
| 46-28,109 | 8/1971 | Japan | 424/303 |
| 763,980 | 12/1956 | United Kingdom | 260/456 A |

*Primary Examiner*—Joseph E. Evans
*Attorney, Agent, or Firm*—Michael C. Sudol, Jr.

[57] ABSTRACT

Substituted 2-aminomethylphenyl sulfamates and pharmaceutically acceptable acid addition salts wherein the sulfamate group is N-substituted with up to 2 groups and the phenyl nucleus is further substituted by from 2 to 4 nuclear substituents which are useful as diuretics and saluretics are disclosed. The products may be prepared by reacting a N-protected substituted 2-aminomethylphenol with a substituted sulfamoyl chloride to generate an intermediate which is N-deblocked to give the compounds of this invention.

10 Claims, No Drawings

SUBSTITUTED 2-AMINOMETHYLPHENYL SULFAMATES

SUMMARY OF THE INVENTION

This invention relates to novel substituted 2-aminomethylphenyl sulfamates and pharmaceutically acceptable acid addition salts wherein the sulfamate group is N-substituted with up to 2 groups and the phenyl nucleus is further substituted by from 2 to 4 nuclear substituents which are useful as diuretics and saluretics. The products may be prepared by reacting a N-protected substituted 2-aminomethylphenol with a substituted sulfamoyl chloride to generate an intermediate which is N-deblocked to give the compounds of this invention.

Pharmacological studies indicate that the instant products are effective diuretic and saluretic agents which can be used in the treatment of conditions associated with electrolyte and fluid retention and hypertension. When administered in therapeutic dosages in conventional vehicles the instant products effectively reduce the amount of sodium and chloride ions in the body, lower dangerous excesses of fluid level to acceptable levels and, in general, alleviate conditions usually associated with edema and hypertension.

The substituted 2-aminomethylphenyl sulfamates of this invention are compounds having the following structural formula:

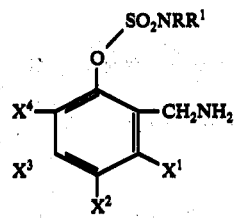

wherein
R is hydrogen, straight or branched chain lower alkyl of 1 to 5 carbon atoms, phenyl or aralkyl of up to 8 carbon atoms such as benzyl;
$R^1$ is hydrogen, straight or branched chain lower alkyl of 1 to 5 carbon atoms, aralkyl of up to 8 carbon atoms such as benzyl, or phenyl;
$X^1$ is hydrogen, lower alkyl of 1 to 3 carbon atoms, or lower alkoxy of 1 to 3 carbon atoms;
$X^2$ is halogen or straight or branched chain lower alkyl wherein the alkyl group has up to 5 carbon atoms;
$X^3$ is hydrogen, halogen, lower alkyl having up to 5 carbon atoms or lower alkoxy having up to 5 carbon atoms;
$X^4$ is halogen;
and the non-toxic pharmaceutically acceptable acid addition salts thereof.

A more preferred aspect of this invention is constituted by those compounds of Formula I wherein:
R is straight or branched chain lower alkyl of 1 to 5 carbon atoms;
$R^1$ is hydrogen, straight or branched chain lower alkyl of 1 to 5 carbon atoms, benzyl or phenyl;
$X^1$ is hydrogen or lower alkoxy of 1 to 3 carbon atoms;
$X^2$ is halogen or branched chain lower alkyl wherein the alkyl group has 3 to 5 carbon atoms;
$X^3$ is hydrogen or lower alkoxy of 1 to 3 carbon atoms;
$X^4$ is chloro, bromo or iodo;
and the non-toxic pharmaceutically acceptable acid addition salts thereof.

A most preferred embodiment of this invention consists of those compounds of Formula I wherein:
R is straight chain lower alkyl of 1 to 3 carbon atoms;
$R^1$ is straight chain lower alkyl of 1 to 3 carbon atoms;
$X^1$ and $X^3$ are hydrogen;
$X^2$ is branched chain lower alkyl wherein the alkyl group has 3 to 5 carbon atoms;
$X^4$ is chloro, bromo or iodo;
and the non-toxic pharmaceutically acceptable acid addition salts thereof.

The non-toxic pharmaceutically acceptable acid addition salts mentioned above are preferably the salts derived from non-toxic pharmaceutically acceptable acids such as hydrochloric acid, hydrobromic acid, hydroiodic acid, sulfuric acid, methanesulfonic acid, isethionic acid and the like.

Preferred specific compounds of this invention can be
2-aminomethyl-4-(1,1-dimethylethyl)-6-iodophenyl N,N-dimethylsulfamate hydrochloride;
2-aminomethyl-4-(1,1-dimethylethyl)-6-bromophenyl N,N-dimethylsulfamate hydrochloride;
2-aminomethyl-4-(1,1-dimethylethyl)-6-chlorophenyl N,N-dimethylsulfamate hydrochloride;
2-aminomethyl-4-(1-methylethyl)-6-iodophenyl N,N-dimethylsulfamate hydrochloride;
2-aminomethyl-4-(1,1-dimethylethyl)-6-iodophenyl N-ethylsulfamate hydrochloride;
2-aminomethyl-3,5-dimethoxy-4,6-dichlorophenyl N,N-dimethylsulfamate hydrochloride;
2-aminomethyl-4-(1,1-dimethylethyl)-6-iodophenyl sulfamate hydrochloride;
2-aminomethyl-4-(1,1-dimethylethyl)-6-iodophenyl N,N-dimethylsulfamate.

The substituted 2-aminomethylphenyl sulfamates of this invention can be prepared according to the following reaction scheme. Method A.

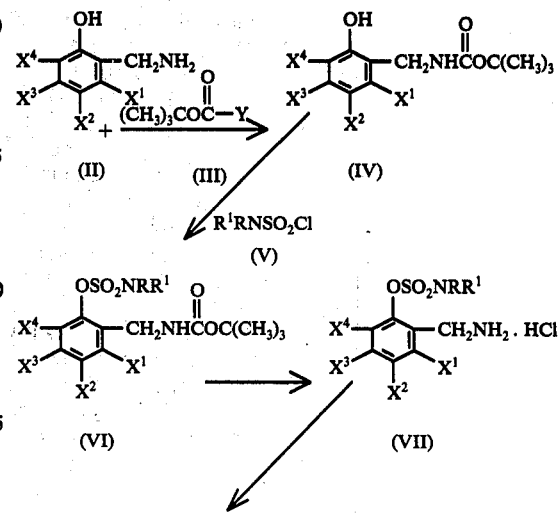

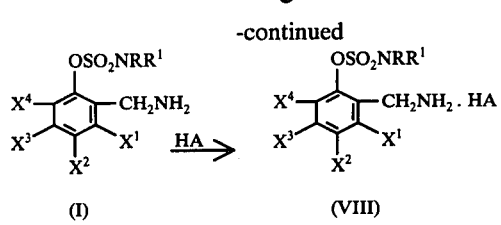

(I)    (VIII)

wherein
R, R¹, X¹, X², X³, and X⁴ are as previously defined;
Y is an azido or 2,4,5-trichlorophenoxy moiety and
HA is a non-toxic pharmaceutically acceptable acid.

In this reaction scheme a substituted 2-aminomethylphenol of Formula II (previously known from U.S. Pat. No. 3,794,734) wherein $X^1$, $X^2$, $X^3$ and $X^4$ are as previously defined is made to react with an activated (1,1-dimethylethyl)oxycarbonyl containing reagent of Formula III wherein Y is as previously defined in the presence of a suitable base, preferably triethylamine when Y is the 2,4,5-trichlorophenoxy moiety and magnesium oxide when Y is the azido group, in a suitable inert solvent, preferably aqueous tetrahydrofuran, at a temperature of 20° C to the reflux temperature of the solvent, preferably 55° to 65° C, for a period of 6 to 36 hours, preferably 18 to 24 hours, to give the N-protected substituted phenol of Formula IV upon dilution of the reaction mixture with water.

The N-protected substituted phenol of Formula IV wherein $X^1$, $X^2$, $X^3$ and $X^4$ are as previously defined is then made to react with a substituted sulfamoyl chloride of Formula V wherein R and R¹ are as previously defined in the presence of a suitable base such as triethylamine, pyridine and the like, preferably triethylamine, in a dry, inert solvent such as methylene chloride, chloroform, tetrahydrofuran and the like, preferably methylene chloride, at a temperature of 0° to 40° C, preferably 20° to 25° C, for a period of 6 to 72 hours, preferably 48 to 72 hours under an inert atmosphere such as nitrogen and the like to give a N-protected substituted phenyl sulfamate intermediate of Formula VI wherein R, R¹, $X^1$, $X^2$, $X^3$ and $X^4$ are as previously defined.

The N-protected substituted phenyl sulfamate of Formula VI is then treated with a suitable protic, acidic medium, preferably either ethanolic hydrochloric acid or trifluoroacetic acid, at a temperature of 0° to 40° C until N-deprotection is complete to give the hydrochloride salt of Formula VII wherein R, R¹, $X^1$, $X^2$, $X^3$ and $X^4$ are as previously defined. When ethanolic hydrochloric acid is used, this reaction is carried out preferably at 20° to 25° C for a period of 1 to 8 hours, preferably 2 to 3 hours, to give the hydrochloride salt of Formula I (i.e., Formula VII) directly upon evaporation of the reaction mixture. When trifluoroacetic acid is used, this reaction is effected preferably at 20° to 25° C for a period of 2 to 30 minutes, preferably 5 to 10 minutes, to give a residue upon removal of the solvent which is treated with ethereal hydrochloric acid to provide the hydrochloride salt of Formula VII.

The hydrochloride salt of Formula VII is readily converted to the free amine of Formula I (wherein R, R¹, $X^1$, $X^2$, $X^3$ and $X^4$ are as previously defined) by methods well known in the art such as dissolution of the hydrochloride salt of Formula VII in water and addition of ammonium hydroxide to the resulting solution whereupon the free amine of Formula I precipitates and is collected by filtration.

Likewise, the free base of Formula I is readily converted to the non-toxic pharmaceutically acceptable acid addition salt of Formula VIII wherein R, R¹, $X^1$, $X^2$, $X^3$ and $X^4$ are as previously defined and HA is a non-toxic pharmaceutically acceptable acid as previously defined by methods well known in the art such as addition of HA to a solution of the free base of Formula I in ethanol-ether whereupon the acid addition salt of Formula VIII is deposited and is collected by filtration.

A subgroup of compounds of this invention of Formula IX

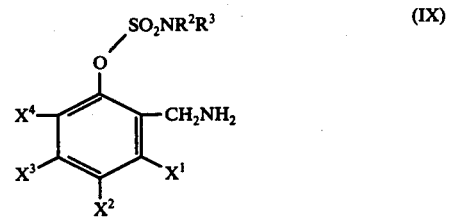

wherein R² is straight or branched chain lower alkyl of 1 to 5 carbon atoms, aralkyl of up to 8 carbon atoms or phenyl; R³ is straight or branched chain lower alkyl of 1 to 5 carbon atoms, aralkyl or phenyl; and $X^1$, $X^2$, $X^3$ and $X^4$ are as previously defined can be synthesized by an alternate synthetic method, Method B, which is described below and depicted by the following flow sheet:

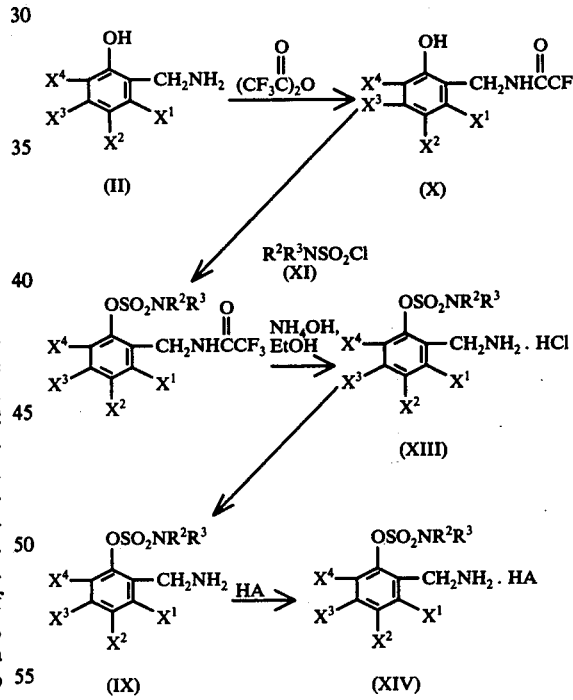

wherein R², R³, $X^1$, $X^2$, $X^3$ and $X^4$ are as above defined for Method B.

A substituted 2-aminomethylphenol of Formula II is treated with excess trifluoroacetic anhydride in an anhydrous inert solvent such as N,N-dimethylformamide, tetrahydrofuran, methylene chloride and the like, preferably N,N-dimethylformamide, at a temperature of 0° to 40° C, preferably 20° to 25° C, for a period of ½ to 2 hours, preferably about 1 hour, to provide a trifluoroacetamide of Formula X wherein $X^1$, $X^2$, $X^3$ and $X^4$ are as previously defined upon work up with water.

The substituted trifluoroacetamide of Formula X wherein $X^1$, $X^2$, $X^3$ and $X^4$ are as previously defined is then made to react with a substituted sulfamoyl chloride of Formula XI wherein $R^2$ and $R^3$ are as previously defined in exactly the same manner as the corresponding step is described in Method A, to give a N-protected substituted phenyl sulfamate of Formula XII wherein $R^2$, $R^3$, $X^1$, $X^2$, $X^3$ and $X^4$ are as previously defined.

The N-protected substituted phenyl sulfamate of Formula XII wherein $R^2$, $R^3$, $X^1$, $X^2$, $X^3$ and $X^4$ are as previously defined is N-deprotected by treatment with a suitable base, preferably ammonium hydroxide, in a suitable inert solvent such as ethanol, methanol, tetrahydrofuran and the like, preferably ethanol, at a temperature of 0° to 40° C, preferably 20° to 25° C, for a period of 24 to 72 hours, preferably about 48 hours. Evaporation of the reaction mixture in vacuo and subsequent treatment of the residue with ethanolic hydrochloric acid provides the hydrochloride salt of Formula XIII wherein $R^2$, $R^3$, $X^1$, $X^2$, $X^3$ and $X^4$ are as previously defined.

The hydrochloride salt of Formula XIII is readily converted to a free base of Formula IX which, in turn, is readily converted to a non-toxic pharmaceutically acceptable acid addition salt of Formula XIV wherein $R^2$, $R^3$, $X^1$, $X^2$, $X^3$, $X^4$ and HA are as previously defined using the same well-known processes respectively described in Method A.

The examples which follow illustrate the substituted 2-aminomethylphenyl sulfamates of this invention and the methods by which they are prepared.

EXAMPLE 1

Preparation of
2-aminomethyl-4-(1,1-dimethylethyl)-6-iodophenyl
N,N-dimethylsulfamate hydrochloride Step A. Preparation of 1,1-Dimethylethyl N-[2-hydroxy-3-iodo-5-(1,1-dimethylethyl)phenylmethyl]-carbamate To a solution of 2-aminomethyl-4-(1,1-dimethylethyl)-6-iodophenol (12 g., 0.04 mole) in tetrahydrofuranwater (10:3; v:v; 130 ml.) is added 1,1-dimethylethyl-2,4,5-trichlorophenyl carbonate (13 g., 0.044 mole) and triethylamine (4.44 g., 0.044 mole). The resulting pale yellow solution is stirred and heated at 60°-65° C for 24 hours, cooled to 20° C and diluted with water (700 ml.). The solid which precipitates is collected, air-dried, triturated with petroleum ether and dried to give 1,1-dimethylethyl N-[2-hydroxy-3-iodo-5-(1,1-dimethylethyl)phenylmethyl]carbamate as a colorless solid (14.3 g., 88%), m.p. 196°-197° with dec. Recrystallization from ethyl acetate affords an analytical sample of 1,1-dimethylethyl N-[2-hydroxy-3-iodo-5-(1,1-dimethylethyl)phenylmethyl]carbamate as a colorless crystals, m.p. 199°-200° with dec.

Step A¹. Alternate Preparation of 1,1-Dimethylethyl N-[2-hydroxy-3-iodo-5-(1,1-dimethylethyl)phenylmethyl]carbamate This compound is prepared essentially by the same method as described in Step A above except that the 1,1-dimethylethyl 2,4,5-trichlorophenyl carbonate is replaced by (1,1-dimethylethyl)oxycarbonyl azide and the triethylamine is replaced by magnesium oxide. The following reagents are employed:

2-aminomethyl-4-(1,1-dimethylethyl)-6-iodophenol
—6 g., 0.02 mole (1,1-dimethylethyl)oxycarbonyl azide —5.72 g., 0.04 mole magnesium oxide —1.6 g., 0.04 mole tetrahydrofuran —80 ml.

water —20 ml.

1,1-Dimethylethyl N-[2-hydroxy-3-iodo-5-(1,1-dimethylethyl)phenylmethyl]carbamate is obtained as a colorless solid (6.5 g., 80%), m.p. 192°-195° C with dec., which upon recrystallization from ethyl acetate provides analytically pure 1,1-dimethylethyl N-[2-hydroxy-3-iodo-5-(1,1-dimethylethyl)phenylmethyl]-carbamate, m.p. 199°-200° C with dec., which is identical with an authentic sample, mixed m.p. 199°-200° with dec.

Step B. Preparation of 2-aminomethyl-4-(1,1-dimethylethyl)-6-iodophenyl N,N-dimethylsulfamate hydrochloride To a solution of N,N-dimethylsulfamoyl chloride (8.7 g., 0.06 mole) in dry methylene chloride (25 ml.) maintained under a nitrogen atmosphere is added slowly and with good stirring a solution of 1,1-dimethylethyl N-[2-hydroxy-3-iodo-5-(1,1-dimethylethyl)phenylmethyl]-carbamate (4 g., 0.01 mole) and triethylamine (6.06 g., 0.06 mole) in dry methylene chloride (100 ml.) at 20°-25° C. The resulting reaction mixture is protected from atmospheric moisture with a calcium chloride drying tube and stirring is maintained at 20°-25° C for 72 hours. Evaporation of the solvent leaves a residual solid which is washed with water and extracted with ether. The organic extract is washed with water and saturated brine, dried over sodium sulfate and filtered. The filtrate is evaporated in vacuo (rotary evaporator) to provide a pale yellow oil which slowly solidifies upon storage at 60°-80° C in a high vacuum (0.1 mm.) for 2 hours to give a colorless solid (6.9 g.), m.p. 114°-118° C. A slurry of the latter in n-hexane (50 ml.) is stirred at 20°-25° C for ½ hour, cooled to 5° C and filtered to yield 3.3 g. (63%) of the intermediate 2-[1,1-dimethylethyl)oxycarbonylaminomethyl]-4-(1,1-dimethylethyl)-6-iodophenyl N,N-dimethylsulfamate, m.p. 118°-120° C.

A solution of the latter (3.3 g., 6.4 millimole) in ethanol (150 ml.) is treated with 12N hydrochloric acid (20 ml.) and stirred at 20°-25° C for 3 hours. Removal of the solvents in vacuo leaves a residual solid which is triturated with ether, collected, washed with ether and air-dried to give 2-aminomethyl-4-(1,1-dimethylethyl)-6-iodophenyl N,N-dimethylsulfamate hydrochloride as a colorless solid (2.5 g., 80%), m.p. 238°-239° C with dec.. Recrystallization of the latter from ethanol-ether (1:3; v:v) affords analytically pure 2-aminomethyl-4-(1,1-dimethylethyl)-6-iodophenyl N,N-dimethylsulfamate hydrochloride, m.p. 239°-240° C with dec.. Hence, Step B yields 2-aminomethyl-4-(1,1-dimethylethyl)-6-iodophenyl N,N-dimethylsulfamate hydrochloride in 49% overall yield.

EXAMPLE 2

Alternate Preparation of
2-aminomethyl-4-(1,1-dimethylethyl)-6-iodophenyl
N,N-dimethylsulfamate hydrochloride Step A. Preparation of 2,2,2-Trifluoro-N-[2-hydroxy-3-iodo-5-(1,1-dimethylethyl)phenylmethyl]-acetamide To a fine suspension of 2-aminomethyl-4-(1,1-dimethylethyl)-6-iodophenol (9 g., 0.03 mole) in dry N,N-dimethylformamide (20 ml.) at 20°-25° C and with vigorous stirring is added dropwise trifluoroacetic anhydride (12.6 g.) 0.06 mole) over 15 to 20 minutes. The resulting clear solution is stirred at ambient temperature for 1 hour and poured into water (500 ml.) providing a heterogeneous mixture which is stirred at 20°–25° C for 2 hours. The insoluble solid is collected, washed with water and crystallized from acetic acid-water (5:2; v:v) to give 2,2,2-trifluoro-N-[2-hydroxy-3-iodo-5-(1,1-dimethylethyl)phenylmethyl]acetamide as a colorless solid (11 g., 91%), m.p. 118°–119° C.

Step B. Preparation of 2-aminomethyl-4-(1,1-dimethylethyl)-6-iodophenyl N,N-dimethylsulfamate hydrochloride To a solution of N,N-dimethylsulfamoyl chloride (17.4 g., 0.12 mole) in dry methylene chloride (75 ml.) maintained under a nitrogen atmosphere is added slowly and with good stirring a solution of 2,2,2-trifluoro-N-[2-hydroxy-3-iodo-5-(1,1-dimethylethyl)-phenylmethyl]acetamide (8 g., 0.02 mole) and triethylamine (12.12 g., 0.12 mole) in dry methylene chloride (200 ml.) at 20°–25° C. The resulting reaction mixture is stirred at 20°–25° C under nitrogen for 72 hours. Removal of the solvent in vacuo leaves a tacky residue which is partitioned between ether and water. The phases are separated and the organic phase is washed successively with 2N hydrochloric acid, water and saturated brine, dried over sodium sulfate and filtered. Evaporation of the filtrate leaves the intermediate 2-(2,2,2-trifluoroacetamidomethyl)-4-(1,1-dimethylethyl)-6-iodophenyl N,N-dimethylsulfamate as a tan oil (10.3 g., 100%).

A solution of the latter (10.3 g., 0.02 mole) in ethanol (40 ml.) is treated with conc. ammonium hydroxide (20 ml.) and stored at 20°–25° C for 44 hours. The resulting reaction mixture is evaporated in vacuo leaving a residual solid which is dissolved in ethanol (200 ml.). The resulting solution is treated with con. hydrochloric acid (2 ml.) and evaporated in vacuo. Trituration of the residual solid with ether affords 2-aminomethyl-4-(1,1-dimethylethyl)-6-iodophenyl N,N-dimethylsulfamate hydrochloride as a colorless solid (4.9 g., 55%), m.p. 238°–239° C with dec., which is identical with the authentic sample prepared in Example 1, Step B; mixed m.p. 238°–239° C with dec.

EXAMPLE 3

Preparation of 2-aminomethyl-4-(1,1-dimethylethyl)-6-chlorophenyl N,N-dimethylsulfamate hydrochloride Step A: Preparation of 1,1-dimethylethyl N-[2-hydroxy-3-chloro-5-(1,1-dimethylethyl)phenylmethyl]carbamate This compound is prepared essentially by the same method as described in Example 1, Step A, except that the 2-aminomethyl-4-(1,1-dimethylethyl)-6-iodophenol is replaced by 2-aminomethyl-4-(1,1-dimethylethyl)-6-chlorophenol. The following reagents are employed:
2-aminomethyl-4-(1,1-dimethylethyl)-6-chlorophenol —3.1 g., 0.014 mole
1,1-dimethylethyl 2,4,5-trichlorophenyl carbonate —4.43 g., 0.015 mole
triethylamine —1.51 g., 0.015 mole
tetrahydrofuran —150 ml.
water —30 ml.

This procedure affords 1,1-dimethylethyl N-[2-hydroxy-3-chloro-5-(1,1-dimethylethyl)phenylmethyl]carbamate as a solid (4.4 g., 100%), m.p. 161°–163° C, which upon crystallization from ethyl acetate provides analytically pure 1,1-dimethylethyl N-[2-hydroxy-3-chloro-5-(1,1dimethylethyl)phenylmethyl]carbamate as colorless crystals, m.p. 161.5°–162.5° C.

Step B. Preparation of 2-aminomethyl-4-(1,1-dimethylethyl)-6-chlorophenyl N,N-dimethylsulfamate hydrochloride This compound is prepared essentially by the same method as described in Example 1, Step B, except that the 1,1-dimethylethyl N-[2-hydroxy-3-iodo-5-(1,1-dimethylethyl)phenylmethyl]carbamate is replaced by 1,1-dimethylethyl N-[2-hydroxy-3-chloro-5-(1,1-dimethylethyl)phenylmethyl]carbamate. The following reagents are employed:
1,1-dimethylethyl N-[2-hydroxy-3-chloro-5-(1,1-dimethylethyl)phenylmethyl]carbamate —3.1 g., 0.01 mole
N,N-dimethylsulfamoyl chloride —5.8 g., 0.04 mole
triethylamine —4 g., 0.04 mole
dry methylene chloride —50 ml.

This procedure yields the intermediate 2-[(1,1-dimethylethyl)oxycarbonylaminomethyl]-4-(1,1-dimethylethyl)-6-chlorophenyl N,N-dimethylsulfamate (2.7 g., 64%), m.p. 122°–123° C, which is converted to 2-aminomethyl-4-(1,1-dimethylethyl)-6-chlorophenyl N,N-dimethylsulfamate hydrochloride with ethanol (150 ml.) and 12N hydrochloric acid (20 ml.) exactly as described in Example 1, Step B. Thereby is obtained 2-aminomethyl-4-(1,1-dimethylethyl)-6-chlorophenyl N,N-dimethylsulfamate hydrochloride as a beige solid (2 g., 56% overall), m.p. 255°–256° C, which upon crystallization from ethanol-ether (2:1; v:v) affords analytically pure 2-aminomethyl-4-(1,1-dimethylethyl)-6-chlorophenyl N,N-dimethylsulfamate hydrochloride as colorless crystals, m.p. 258.5°–259° C.

EXAMPLE 4

Preparation of 2-Aminomethyl-4-(1,1-dimethylethyl)-6-bromophenyl N,N-dimethylsulfamate hydrochloride By following essentially the same procedures described in Example 1 but beginning with 2-aminomethyl-4-(1,1-dimethylethyl)-6-bromophenol instead of 2-aminomethyl-4-(1,1-dimethylethyl)-6-iodophenol, there are obtained successively:
Step A, 1,1-dimethylethyl N-[2-hydroxy-3-bromo-5-(1,1-dimethylethyl)-phenylmethyl]carbamate;
Step B, 2-[(1,1-dimethylethyl)oxycarbonylaminomethyl]-4-(1,1-dimethylethyl)-6-bromophenyl N,N-dimethylsulfamate as an intermediate; and
2-aminomethyl-4-(1,1-dimethylethyl)-6-bromophenyl N,N-dimethylsulfamate hydrochloride.

EXAMPLE 5

Preparation of 2-Aminomethyl-4-(1-methylethyl)-6-iodophenyl N,N-dimethylsulfamate hydrochloride By following essentially the same procedures described in Example 1 but beginning with 2-aminomethyl-4-(1-methylethyl)-6-iodophenol instead of 2-aminomethyl-4-(1,1-dimethylethyl)-6-iodophenol, there are obtained successively:
Step A, 1,1-dimethylethyl N-[2-hydroxy-3-iodo-5-(1-methylethyl)-phenylmethyl]carbamate;

Step B, 2-[(1,1-dimethylethyl)oxycarbonylaminomethyl]-4-(1-methylethyl)-6-iodophenyl N,N-dimethylsulfamate as an intermediate; and 2-aminomethyl-4-(1-methylethyl)-6-iodophenyl N,N-dimethylsulfamate hydrochloride.

EXAMPLE 6

Preparation of
2-Aminomethyl-4-(1-methylpropyl)-6-chlorophenyl N,N-dimethylsulfamate hydrochloride By following essentially the same procedures described in Example 3 but beginning with 2-aminomethyl-4-(1-methylpropyl)-6-chlorophenol instead of 2-aminomethyl-4-(1,1-dimethylethyl)-6-chlorophenol, there are obtained successively:

Step A, 1,1-dimethylethyl N-[2-hydroxy-3-chloro-5-(1-methylpropyl)-phenylmethyl]carbamate;

Step B, 2-[(1,1-dimethylethyl)oxycarbonylaminomethyl]-4-(1-methylpropyl)-6-chlorophenyl N,N-dimethylsulfamate as an intermediate; and 2-aminomethyl-4-(1-methylpropyl)-6-chlorophenyl N,N-dimethylsulfamate hydrochloride.

EXAMPLE 7

Preparation of
2-Aminomethyl-4-(1,1-dimethylethyl)-6-iodo phenyl N-ethylsulfamate hydrochloride This compound is prepared essentially by the method described in Example 1, Step B, except that the N,N-dimethylsulfamoyl chloride is replaced by N-ethylsulfamoyl chloride. The following reagents are employed:

1,1-dimethylethyl N-[2-hydroxy-3-iodo-5-(1,1-dimethylethyl)phenylmethyl]carbamate —14.45 g., 0.036 mole N-ethylsulfamoyl chloride —31 g., 0.22 mole triethylamine —21.7 g., 0.22 mole dry methylene chloride —490 ml.

This procedure gives the intermediate 2-[(1,1-dimethylethyl)oxycarbonylaminomethyl]-4-(1,1-dimethylethyl)-6-iodophenyl N-ethylsulfamate as a tacky, yellow semi-solid which is converted to 2-aminomethyl-4-(1,1-dimethylethyl)-6-iodophenyl N-ethylsulfamate hydrochloride with ethanol (150 ml.) and 12N hydrochloric acid (15 ml.) exactly as described in Example 1, Step B. Thereby is obtained 2-aminomethyl-4-(1,1-dimethylethyl)-6-iodophenyl N-ethylsulfamate hydrochloride as an off-white solid (5.3 g., 35%), m.p. 168°-168.5° C with dec., which crystallizes from ethanol-ether (1:10; v:v) as colorless crystals of analytically pure 2-aminomethyl-4-(1,1-dimethylethyl)-6-iodophenyl N-ethylsulfamate hydrochloride, m.p. 168°-168.5° (unchanged) with dec.

EXAMPLE 8

Preparation of
2-Aminomethyl-4-(1,1-dimethylethyl)-6-iodophenyl N-phenylsulfamate hydrochloride This compound is prepared essentially by the method described in Example 1, Step B, except that the N,N-dimethylsulfamoyl chloride is replaced by N-phenylsulfamoyl chloride.

The following reagents are employed:

1,1-dimethylethyl N-[2-hydroxy-3-iodo-5-(1,1-dimethylethyl)phenylmethyl]carbamate —4.0 g., 0.01 mole N-phenylsulfamoyl chloride —3.8 g., 0.02 mole triethylamine —2.02 g., 0.02 mole dry methylene chloride —140 ml.

This procedure provides 2-[(1,1-dimethylethyl)oxycarbonylaminomethyl]-4-(1,1-dimethylethyl)-6-iodophenyl N-phenylsulfamate as a synthetic intermediate which is converted to 2-aminomethyl-4-(1,1-dimethylethyl)-6-iodophenyl N-phenylsulfamate hydrochloride with ethanol (50 ml.) and 12N hydrochloric acid (5 ml.) exactly as described in Example 1, Step B. Thereby is obtained crude 2-aminomethyl-4-(1,1-dimethylethyl)-6-iodophenyl N-phenylsulfamate hydrochloride as a colorless solid (2 g., 40%), m.p. 148°-160° C with dec. which upon crystallization from p-dioxane-ether (1:5; v:v) yields analytically pure 2-aminomethyl-4-(1,1-dimethylethyl)-6-iodophenyl N-phenylsulfamate hydrochloride as colorless crystals, m.p. 150°-152° C with dec.

EXAMPLE 9

Preparation of
2-Aminomethyl-3,5-dimethoxy-4,6-dichlorophenyl N,N-dimethylsulfamate hydrochloride By following essentially the same procedures described in Example 1 but beginning with 2-aminomethyl-3,5-dimethoxy-4,6-dichlorophenol instead of 2-aminomethyl-4-(1,1-dimethylethyl)-6-iodophenol, there are obtained successively:

Step A, 1,1-dimethylethyl N-(2-hydroxy-3,5-dichloro-4,6-dimethoxyphenylmethyl)carbamate;

Step B, 2-[(1,1-dimethylethyl)oxycarbonylaminomethyl]-3,5-dimethoxy-4,6-dichlorophenyl N,N-dimethylsulfamate as an intermediate; and 2-aminomethyl-3,5-dimethoxy-4,6-dichlorophenyl N,N-dimethylsulfamate hydrochloride.

EXAMPLE 10

Preparation of
2-Aminomethyl-4-(1,1-dimethylethyl)-6-iodophenyl sulfamate hydrochloride This compound is prepared essentially by the same method as described in Example 1, Step B, except that the N,N-dimethylsulfamoyl chloride is replaced by N-(1,1-dimethylethyl)sulfamoyl chloride and trifluoroacetic acid is used to generate the final product rather than ethanol-12N hyrochloric acid (10:1; v:v). The following reagents are employed.

1,1-dimethylethyl N-[2-hydroxy-3-iodo-5-(1,1-dimethylethyl)phenylmethyl]carbamate —4.0 g., 0.01 mole N-(1,1-dimethylethyl)sulfamoyl chloride —4.0 g., 0.023 mole triethylamine —2.36 g., 0.023 mole dry methylene chloride —140 ml.

This procedure provides 2-[(1,1-dimethylethyl)oxycarbonylaminomethyl]-4-(1,1-dimethylethyl)-6-iodophenyl N-(1,1-dimethylethyl)sulfamate as a synthetic intermediate (6.15 g.) which is dissolved in trifluoroacetic acid (40 ml.). The resulting solution is stirred and heated at 50°-60° C for ½ hour and evaporated in vacuo leaving an oily residue. The residue is dissolved in ether (30 ml.) providing a clear solution which is treated with 12N hydrochloric acid (1 ml.) and evaporated in vacuo to afford a residual solid. The solid is triturated at 20° C with ether, collected and dried to give 2-aminomethyl-4-(1,1-dimethylethyl)-6-iodophenyl sulfamate hydrochloride as a pale tan solid (1.9 g., 45.2%), m.p. 173°-174° with dec.

EXAMPLE 11

Preparation of
2-Aminomethyl-4-(1,1-dimethylethyl)-6-iodophenyl
N,N-dimethylsulfamate To a solution of 2-aminomethyl-4-(1,1-dimethylethyl)-6-iodophenyl N,N-dimethylsulfamate hydrochloride (100 mg., 0.22 millimole) in water (30 ml.) is added 15N ammonium hydroxide (1 ml.). The resulting heterogeneous mixture is stirred at 20° C for 5 minutes and decanted. Trituration of the insoluble gummy residue with petroleum ether provides a colorless solid which is collected, washed with petroleum ether and dried to afford 65 mg. (73%) of 2-aminomethyl-4-(1,1-dimethylethyl)-6-iodophenyl N,N-dimethyl sulfamate, m.p. 94°-95° C.

EXAMPLE 12

Preparation of
2-Aminomethyl-4-(1,1-dimethylethyl)-6-iodophenyl
N,N-dimethylsulfamate hydrobromide To a solution of 2-aminomethyl-4-(1,1-dimethylethyl)-6-iodophenyl N,N-dimethylsulfamate (65 mg., 0.16 millimole) in ethanol (2 ml.) is added slowly with stirring 48% hydrobromic acid (0.5 ml.) at 20° C. After standing at 20° C for 15 minutes, the deposited solid is collected and dried to give 2-aminomethyl-4-(1,1-dimethylethyl)-6-iodophenyl N,N-dimethylsulfamate hydrobromide as a colorless solid (70 mg., 89%), m.p. 243°-244° C with dec.

The novel compounds of this invention are diuretic and saluretic agents which can be administered in a wide variety of therapeutic dosages in conventional vehicles as, for example, by oral administration in the form of a tablet or by intravenous injection. Also, the daily dosage of the products may be varied over a wide range varying from 5 to 2,000 mg. The product is preferably administered in subdivided doses in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products which may be administered in a total daily dosage of from 100 mg. to 2,000 mg. in a pharmaceutically acceptable carrier.

A suitable unit dosage form of the products of this invention can be administered by mixing 50 milligrams of a substituted 2-aminomethylphenyl sulfamate (I) or a suitable salt thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods and, if desired, can be made up as elixirs or as injectable solutions by methods well known to pharmacists.

The following example is included to illustrate the preparation of a representative dosage form:

EXAMPLE 13

Dry-filled capsules containing 50 mg. of active ingredient per capsule

|  | Per Capsule |
|---|---|
| 2-aminomethyl-4-(1,1-dimethylethyl)-6-iodophenyl N,N-dimethylsulfamate hydrochloride | 50 mg. |
| lactose | 149 mg. |
| magnesium stearate | 1 mg. |
| Capsule (Size No. 1) | 200 mg. |

The 2-aminomethyl-4-(1,1-dimethylethyl)-6-iodophenyl N,N-dimethylsulfamate hydrochloride is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

What is claimed is:

1. A compound of the formula:

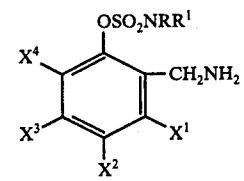

wherein
R is hydrogen, straight or branched chain lower alkyl of 1–5 carbon atoms, aralkyl up to 8 carbon atoms or phenyl;
$R^1$ is hydrogen, straight or branched chain lower alkyl of 1 to 5 carbon atoms, aralkyl of up to 8 carbon atoms or phenyl;
$X^1$ is hydrogen, lower alkyl of 1 to 3 carbon atoms or lower alkoxy of 1 to 3 carbon atoms;
$X^2$ is halogen or straight or branched chain lower alkyl wherein the alkyl group has up to 5 carbon atoms;
$X^3$ is hydrogen, halogen, lower alkyl having up to 5 carbon atoms or lower alkoxy having up to 5 carbon atoms;
$X^4$ is halogen;
and the non-toxic pharmaceutically acceptable salts thereof.

2. A compound of the formula:

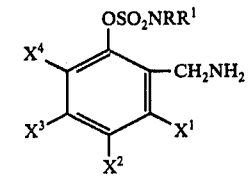

wherein
R is a straight or branched chain lower alkyl having 1 to 5 carbon atoms;
$R^1$ is hydrogen, straight or branched chain lower alkyl having from 1 to 5 carbon atoms, benzyl or phenyl;
$X^1$ is hydrogen or lower alkoxy of 1–3 carbon atoms;

$X^2$ is halogen or a branched chain lower alkyl from 3 to 5 carbon atoms;

$X^3$ is hydrogen or lower alkoxy having from 1 to 3 carbon atoms;

$X^4$ is chloro, bromo or iodo; and the non-toxic pharmaceutically acceptable salts thereof.

3. A compound of the formula:

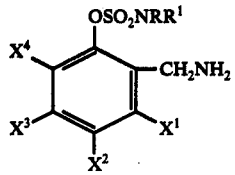

wherein

R is a straight chain lower alkyl of 1 to 3 carbon atoms;

$R^1$ is a straight chain lower alkyl of 1 to 3 carbon atoms;

$X^1$ and $X^3$ are hydrogen;

$X^2$ is a branched chain lower alkyl having from 3 to 5 carbon atoms;

$X^4$ is chloro, bromo or iodo; and the non-toxic pharmaceutically acceptable acid addition salts thereof.

4. A compound according to claim 1 being 2-aminomethyl-4-(1,1-dimethylethyl)-6-iodophenyl sulfamate hydrochloride.

5. A compound according to claim 1 being 2-aminomethyl-4-(1,1-dimethylethyl)-6-iodophenyl N,N-dimethylsulfamate.

6. A compound according to claim 1 being 2-aminomethyl-4-(1,1-dimethylethyl)-6-iodophenyl N,N-dimethylsulfamate hydrochloride.

7. A compound according to claim 1 being 2-aminomethyl-4-(1,1-dimethylethyl)-6-bromophenyl N,N-dimethylsulfamate hydrochloride.

8. A compound according to claim 1 being 2-aminomethyl-4-(1,1-dimethylethyl)-6-chlorophenyl N,N-dimethylsulfamate hydrochloride.

9. A pharmaceutical composition useful in the treatment of edema and hypertension which comprises 50 to 500 mg. of a compound of the formula:

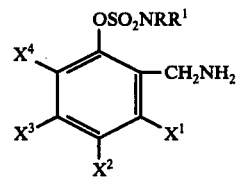

wherein

R is hydrogen, straight or branched chain lower alkyl of 1–5 carbon atoms, aralkyl up to 8 carbon atoms or phenyl;

$R^1$ is hydrogen, straight or branched chain lower alkyl of 1 to 5 carbon atoms, aralkyl of up to 8 carbon atoms or phenyl;

$X^1$ is hydrogen, lower alkyl of 1 to 3 carbon atoms or lower alkoxy of 1 to 3 carbon atoms;

$X^2$ is halogen or straight or branched chain lower alkyl wherein the alkyl group has up to 5 carbon atoms;

$X^3$ is hydrogen, halogen, lower alkyl having up to 5 carbon atoms or lower alkoxy having up to 5 carbon atoms;

$X^4$ is halogen;

and the non-toxic pharmaceutically acceptable salts thereof and a pharmaceutically acceptable carrier.

10. A method for the treatment of edema and hypertension which comprises administering a unitary dosage of a compound of the formula:

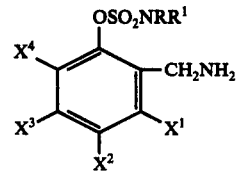

wherein

R is hydrogen, straight or branched chain lower alkyl of 1–5 carbon atoms, aralkyl up to 8 carbon atoms or phenyl;

$R^1$ is hydrogen, straight or branched chain lower alkyl of 1 to 5 carbon atoms, aralkyl of up to 8 carbon atoms or phenyl;

$X^1$ is hydrogen, lower alkyl of 1 to 3 carbon atoms or lower alkoxy of 1 to 3 carbon atoms;

$X^2$ is halogen or straight or branched chain lower alkyl wherein the alkyl group has up to 5 carbon atoms;

$X^3$ is hydrogen, halogen, lower alkyl having up to 5 carbon atoms or lower alkoxy having up to 5 carbon atoms;

$X^4$ is halogen;

and the non-toxic pharmaceutically acceptable salts thereof.

* * * * *